(12) United States Patent
Wright et al.

(10) Patent No.: US 6,827,707 B2
(45) Date of Patent: Dec. 7, 2004

(54) VENIPUNCTURE SITE PROTECTOR AND METHOD OF USING SAME

(75) Inventors: Clifford A. Wright, San Diego, CA (US); Kion Guold, San Diego, CA (US)

(73) Assignee: Medical Device Group, Inc.

( * ) Notice: Subject to any disclaimer, the term of this patent is extended or adjusted under 35 U.S.C. 154(b) by 90 days.

(21) Appl. No.: 10/360,253

(22) Filed: Feb. 6, 2003

(65) Prior Publication Data

US 2004/0167475 A1 Aug. 26, 2004

(51) Int. Cl.[7] ............................................. A61M 5/32
(52) U.S. Cl. ...................................... 604/180; 604/174
(58) Field of Search ............................... 604/174–180, 604/506–508; 128/DIG. 6, DIG. 26

(56) References Cited

U.S. PATENT DOCUMENTS

| | | | |
|---|---|---|---|
| 2,367,690 A | | 1/1945 | Purdy |
| 3,900,026 A | | 8/1975 | Wagner |
| 3,901,226 A | | 8/1975 | Scardenzan |
| 4,059,105 A | | 11/1977 | Cutruzzula et al. |
| 4,316,461 A | | 2/1982 | Marais et al. |
| 4,633,863 A | | 1/1987 | Filips et al. |
| 4,645,492 A | * | 2/1987 | Weeks .......................... 604/174 |
| 4,679,553 A | | 7/1987 | Proulx et al. |
| 4,781,695 A | | 11/1988 | Dalton |
| 4,846,807 A | | 7/1989 | Safadago |
| 4,870,976 A | | 10/1989 | Denny |
| 4,898,587 A | | 2/1990 | Mera |
| 4,976,698 A | | 12/1990 | Stokley |
| 5,074,847 A | | 12/1991 | Greenwell et al. |
| 5,112,313 A | | 5/1992 | Sallee |
| 5,116,324 A | | 5/1992 | Brierley et al. |
| 5,167,240 A | | 12/1992 | Rozier et al. |
| 5,339,834 A | | 8/1994 | Marcelli |
| 5,413,120 A | | 5/1995 | Grant |
| 5,449,349 A | | 9/1995 | Sallee et al. |
| 5,690,616 A | | 11/1997 | Mogg |
| 5,776,106 A | | 7/1998 | Matyas |
| 5,885,254 A | | 3/1999 | Matyas |
| 6,231,547 B1 | | 5/2001 | O'Hara |
| 6,322,539 B1 | | 11/2001 | Cook |

* cited by examiner

*Primary Examiner*—Kevin C. Sirmons
(74) *Attorney, Agent, or Firm*—Jerry R. Potts (57) ABSTRACT

A venipuncture site protector having a slotted securement, which has mounted thereto, a transparent tapered body member defined by a slotted rear wall at its proximal end and a perforated front wall at its distal end. The rear wall and front wall are integrally connected to a flange having a tube receiving slot that is aligned with another tube receiving slot disposed in the rear wall as well as a slot within the slotted securement. The rear wall and the front wall rise up to a dome apex from which an internal wall depends into the interior space of the dome. The internal wall is disposed between the rear wall and the front wall and includes yet another tube receiving slot that is sufficiently wide to receive therein an I.V. tube associated with an I.V. connected catheter but not sufficiently wide to allow the I.V. connected catheter to pass therethrough.

20 Claims, 10 Drawing Sheets

VENIPUNCTURE SITE PROTECTOR AND METHOD OF USING SAME

FIELD OF THE INVENTION

The present invention relates to a device for protecting an intravenous site of a patient from water and other contaminants during intravenous infusion and more particularly to a device for securing and protecting and intravenous catheter from unwanted and undesired movement thereby significantly decreasing complications and reducing unscheduled catheter restarts.

BACKGROUND

An intravenous catheter can be dangerous if not properly secured—dangerous to both the patient and the healthcare worker. Taping the intravenous catheter to the skin of the patient is not an acceptable solution, as tape is not designed to secure a catheter. Moreover, tape allows micro-movement of a catheter which in turn can result in complications, including phlebitis, infiltration, extravasations, dislodgement, disconnection, and even infection. Such complications necessitate unscheduled catheter restarts—which expose healthcare workers to dangerous blood-filled stylets and needles.

Therefore it would be highly desirable to have a new and improved device and method for securing and protecting and intravenous catheter from unwanted and undesired movement thereby significantly decreasing complications and reducing unscheduled catheter restarts.

SUMMARY OF THE INVENTION

In accordance with one preferred embodiment of the present invention there is provided a venipuncture site protector having a transparent tapered body member having a slotted face at its proximal end disposed at about an angle of 60 degrees and an interior wall for wedging a conventional catheter in a fixed secured position after the catheter has been previously disposed into the vein of a patient.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings wherein.

DETAILED DESCRIPTION OF THE PREFERRED EMBODIMENTS

Before discussing the preferred embodiment of the present invention, it may be helpful to first briefly review the basic devices and concepts used in the administration of fluids and or medications directly into a venous system of a patient, which is otherwise called, intravenous therapy, or simply I.V. therapy.

The most common method of administering I.V. fluids is with an I.V. catheter 8, which generally comprises a catheter C, a needle (not shown), and a catheter head or flashback chamber H which is adapted to be connected to an I.V. set and its associated I.V. tubing T by a luer nut arrangement L. The flowing of blood into the flashback chamber H provides an I.V. technician with a visual indication of a successful venous entry.

Figure 1:
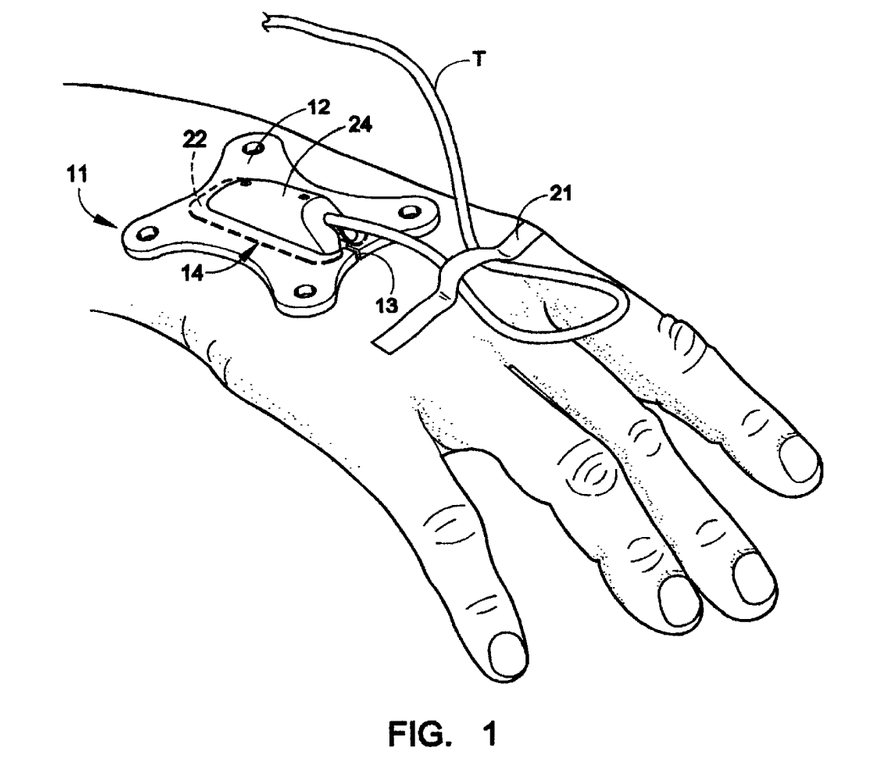
FIG. 1 is a perspective view of a venipuncture site protector, which is constructed in accordance with the present invention.

In use the I.V. technician selects a venous access site, which typically will be the top surface area of a patient's hand as best seen in FIG. 1. Once the I.V. technician has selected and disinfected the venous access site area, the catheter C is then inserted into a located vein within the site area using the needle. The needle is then withdrawn leaving only the semi-flexible catheter C in the vein of the patient. Blood flow into the flashback chamber H provides the I.V. technician with a visual indication that the catheter C has been properly positioned within the vein of the patient.

The I.V. technician then attaches an I.V. fluid set (not shown) and more particularly, the I.V. tubing T to the catheter head H using the luer lock nut arrangement L disposed at the distal end of the I.V. tubing T. The luer lock nut arrangement L includes a catheter connector 9 that is secured to the distal end of the tubing T and which is adapted to be inserted into the flashback chamber H and then locked into a fluid tight seal with a rotatable nut N that slide along the outer surface of the catheter connector 9. In this regard, the connector 9 is inserted into the flashback chamber H and the nut N is pushed along the connector 9 and onto the proximal end of the head H. With the nut N so positioned against the head H, the nut N is rotated into locking engagement. In this process, the I.V. tubing T is connected in a fluid tight seal with the catheter C to facilitate the administration of fluid therapy.

It should be understood by those skilled in the art that the I.V. connector 9 and I.V. catheter 8 are standardized relative to relative to size and overall length. This standardization of size and length is important relative to the preferred embodiment of the present invention as will be explained hereinafter in greater detail.

Referring now to the drawings and more particularly to FIG. 1 thereof there is shown a venipuncture site protector or shielding device 10, which is constructed in accordance with one preferred embodiment of the present invention. The venipuncture site protector 10 is adapted to protect a venipuncture site 20, and more particularly an I.V. connected catheter 8 from unwanted and undesired movement thereby significantly decreasing complications and reducing unscheduled catheter restarts. The term "I.V. connected catheter " as used herein means both the catheter connector 9, the luer lock nut N, the catheter head H, and the exposed proximal end of the catheter C connected at the distal end of the catheter head H, which catheter C was previously inserted into the vein of a patient.

Considering now the venipuncture site protector 10 in greater detail with reference to FIGS. 1–5, the venipuncture site protector 10 generally includes a slotted securement 12 having a slotted partitioned transparent shield or body member 14 and a removable protective cover 17 secured thereto. The body member 14 has an overall length of l, height h, and width dimension w, which dimensions are selected to assure that: 1) a conventional intravenous catheter head H and its associated catheter C (that has been previously disposed into a vein of a patient) and 2) the luer lock arrangement L of an I.V. set (previously connected to the catheter head H) are completely confined within the interior space of the body member 14 and thereby, are protected from accidental contact with an object. As will be explained hereinafter in greater detail, the slotted securement 12 and the slotted partitioned dome cooperate to permit the I.V. connected catheter 8 to be wedged in a friction tight manner against a slotted internal wall 18 disposed within the shield 14 and to releasably capture the I.V. tubing T so that it becomes extremely difficult, if not impossible to move the I.V. connected catheter without first removing the securement 12 from the skin of the patient.

Figure 2:
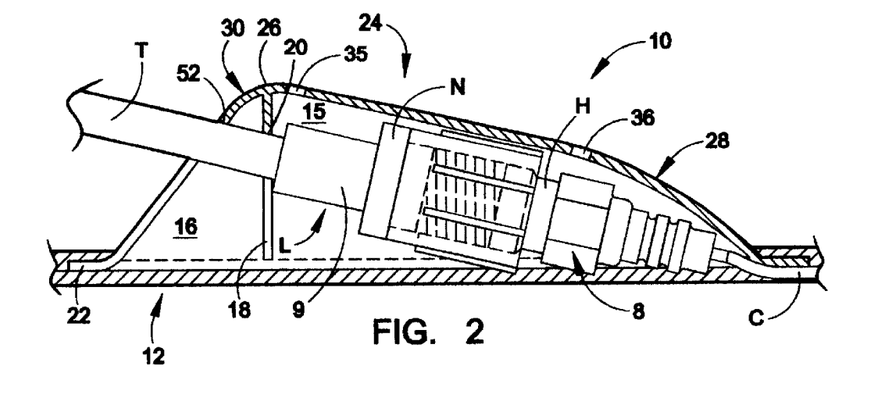
FIG. 2 is side elevational view of the venipuncture site protector of FIG. 1.
Figures 3, 4:
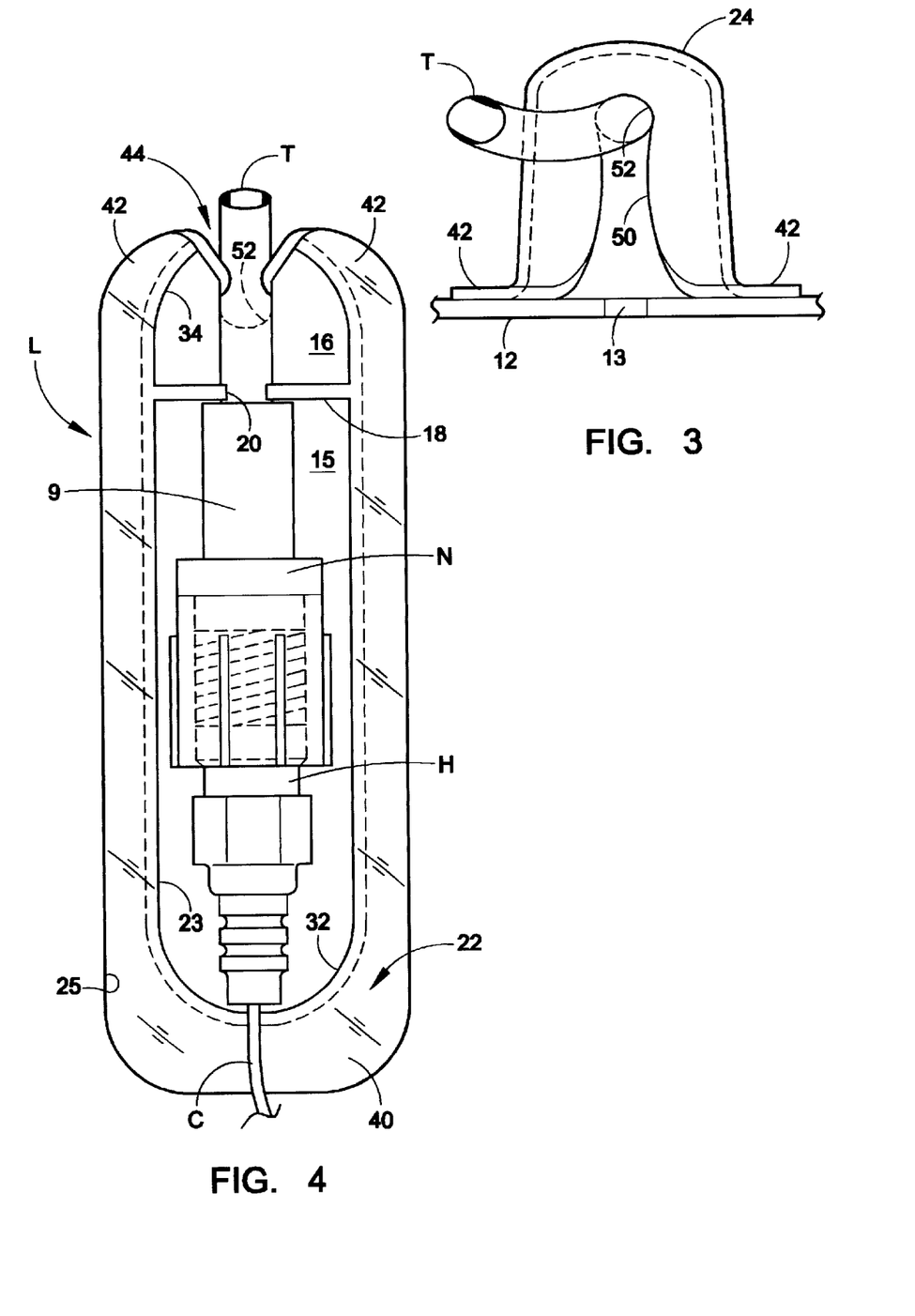
FIG. 3 is front elevational view of the venipuncture site protector of FIG. 1.
FIG. 4 is a bottom plane view of a protective dome illustrated in FIG. 2.
Figure 5:
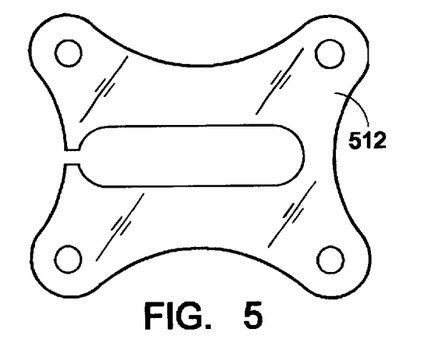
FIG. 5 is a top plane view of a securement forming part of the venipuncture site protector of FIG. 1.
Figure 27:
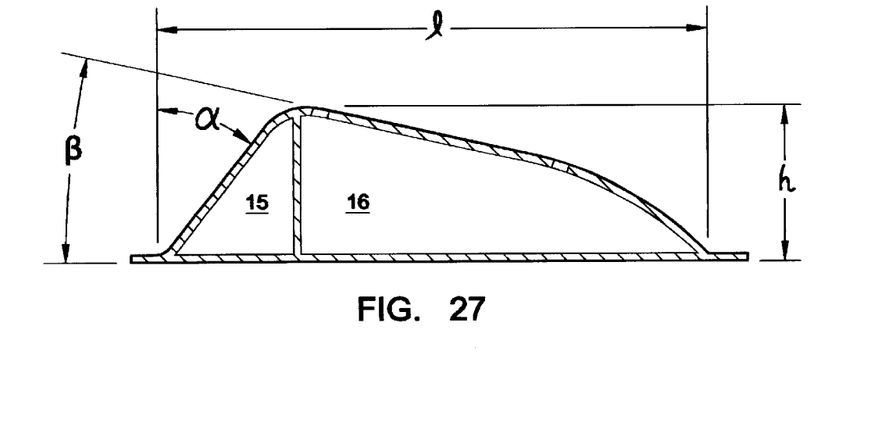
FIG. 27 is a diagrammatic side elevational sectional view of the venipuncture site protector of FIG. 1.

The body member 14 as best seen in FIGS. 2, 4 and 27 has a unitary construction which is defined by a generally rectangularly shaped flange 22 having inner and outer edges 23 and 25 respectively, and a perforated dome 24 which is integrally connected to the flange 22 rising upwardly from the flange inner edge 23 to an apex 26 (FIG. 2).

The flange 22 has a wide rear portion 40 and a narrow front portion 42, which front portion 42 converges to form a tube access slot 44 that is in alignment with another tube access slot 13 that is disposed in a front portion of the securement 12.

The dome 24 is generally triangularly shaped in a side elevational view (FIG. 2) defined by a tapered rear wall portion 28 and a tapered front wall portion 30, which walls 28 and 30 extend upwardly from the flange 22 meeting at the apex 26. The dome 24 from a bottom plane view is generally rectangular with semicircular end segments 32 and 34. As best seen in FIGS. 3–4, the tapered front wall portion 30 includes a tube access slot 50 that extends partially up the wall 30 terminating in a tube stop 52. As best seen in the top plane view of FIG. 4, the tube access slot 50 is in alignment with the tube access slot 44 disposed in the flange 22 and the tube access slot 13 disposed in the securement 12.

Depending perpendicularly downwardly from the dome apex 26 is an internal wall 18 whose side peripheral edges are integrally connected to an interior surface portion of the dome 24. The internal wall 18 divides or partitions the interior space of the body member 14 into a rear space or I.V. connected catheter compartment 15 and a front space or I.V. tubing compartment 16. The internal wall 18 includes a centrally disposed tube receiving slot 19 that terminates at its upper end in a tube receiving stop 20, which is generally circular, and dimension for receiving therein the tubing T of the I.V. set. As best seen in FIGS. 2 and 4, the tube receiving stop 20 is also in general parallel alignment with the tube receiving stop 52 disposed in the front wall 30. In this regard, the two stops 20 and 52 are slightly spaced apart from one another, which is an important feature of the present invention as such spacing help to secure the tubing T of the I.V. set at two different points, one point at the internal wall 18 completely enclosed within the dome 24 and another point at the front wall 30 of the dome 24 so the tubing T can not be easily dislodged once it is captured in the stops 20 and 52 as will be explained hereinafter in greater detail.

Considering now the securement 12 in greater detail with reference to FIGS. 5, 19, 20 and 21, the securement 12 generally includes a base securement 120 with a centrally disposed plug 160, which is adhesively secured to the base securement 120. The plug 160 as will be explained hereinafter in greater detail is utilized to help secure the dome 24 to the base securement 120.

The base securement 120 includes a smooth plastic layer 100, which is coated on its underside with a layer of non-skin irritating adhesive 102. The underside of the plug 160 is also coated with a layer of non-skin irritating adhesive 136. The adhesive layer 102 disposed on the base securement is covered by a pair of spaced apart wax paper covers 104, while the adhesive layer 136 disposed on the plug 160, is covered by another sheet of wax paper 17. The base securement 120 includes an access channel 108, which is aligned with a similar access channel 165 that is disposed at one end of the plug 160. The access channel 108 and 165 cooperate to define the tube access channel or slot 13. As will be explained hereinafter, the protective covers 17 and 104 are removable and are provided to protect the adhesive surfaces 136 and 102 respectively until such time as the securement 12 is ready to be utilized with a patient. It will suffice for the moment to mentioned that the securement 12 is initially or partially secured to the venipuncture site 11 by removing the cover 17 and pressing the adhesive layer 136 against the skin of the patient and then after the I.V. connected catheter has been secured within the dome 24, the securement 12 is fixed in placed by removing the covers 104 to press the uncovered adhesive surfaces 102 against the skin of the patient. This is an important feature of this embodiment of the present invention, as this allows the site protector 10 to remain in place for extended periods of time thereby greatly reducing the risk of exposing healthcare worker to dangerous blood-filled stylets and needles.

Figure 21:
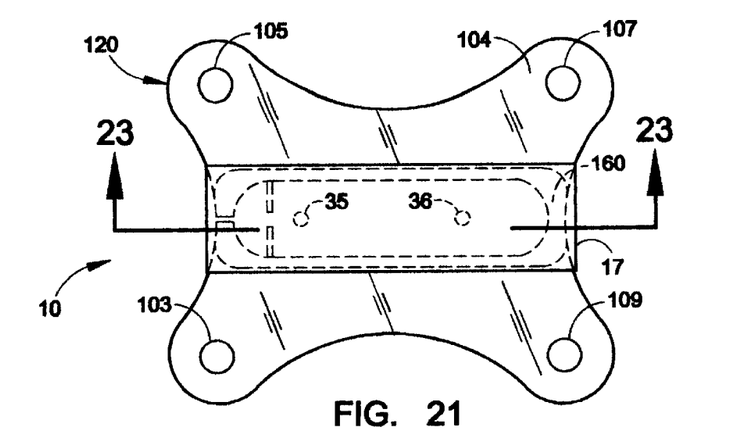
Figure 24:
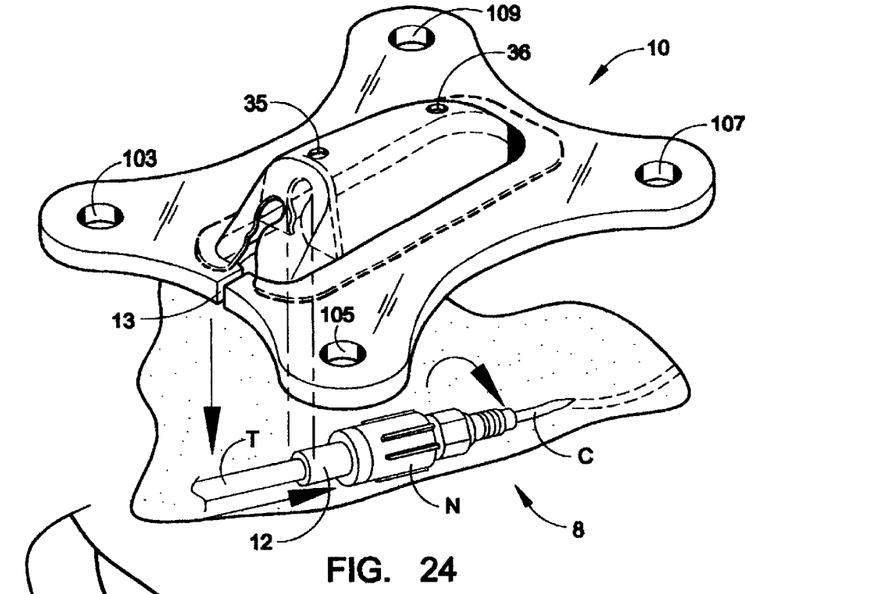
FIGS. 24–26 illustrate the steps of using the venipuncture site protector of FIG. 1.
Figure 25:
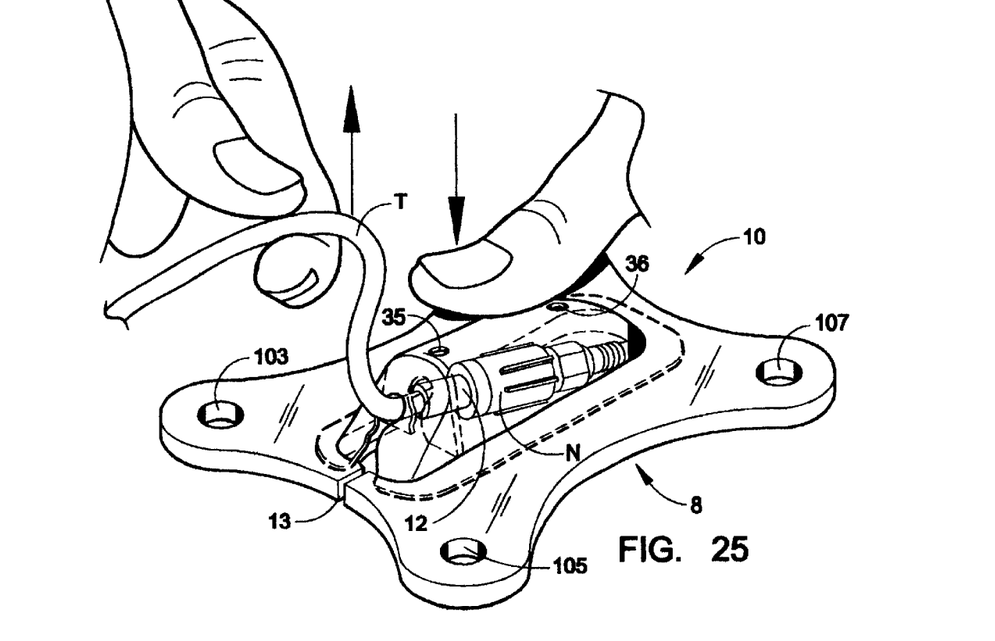

Considering now the novel method of using the site protector 10, as best seen in FIGS. 21 and 24–25 a healthcare provider such as a doctor or a nurse creates a venipuncture site 11 by using an I.V. catheter 8 to insert the catheter C into the vein of a patient.

The I.V. set tubing T is then connected in a fluid tight seal with the catheter C to facilitate the administration of fluid therapy in the manner as previously described. More particularly, the healthcare provider attaches the I.V. set tubing T to the catheter 8 by sliding the nut N along the plastic connector 9 and into engagement with the head H. The nut is then rotated to lock the I.V. set tubing T to the catheter 8 as been seen in FIG. 24.

With the I.V. set tubing T so attached to the catheter 8, the healthcare provider removes the sheet of protective covering 17 from the underside of the venipuncture site protector 10 to provide access to the interior of the shield or body member 14.

Next, the dome 24 is positioned over the venipuncture site 11 in an aligned manner so that the connector 9 is disposed within the front space 15 and against the partition or interior wall 18 and the I.V. set tubing T aligned in the tube access slot 13 of the securement 12, the tube access slot 52 of the front wall 30 and the tube receiving slot 19 of the internal wall 18. With the dome 24 and the tubing T so aligned, the dome 24 of the site protector 10 is pressed against the skin of the patient. In this regard, the unprotected adhesive surface 136 uncovered when the cover 17 was removed secures the site protector 10 to the skin of the patient.

Next as best seen in FIG. 25, the healthcare provider grabs the tubing T extending from the access slot 13 toward the I.V. set in one hand and pulls the tubing T upwardly through the tubing access slot 13 and further upward into the tube access slot 52 of the front wall 30, and further upward into the tube receiving slot 19 of the internal wall 18, while simultaneously pushing down on the top of the dome 24 to hold it in place over the venipuncture site 11. This push and pull action allows a portion of the tubing T to be captured in the tubing receiving stop 20 of the interior wall 18 and in the tube receiving stop 52 of the front wall 30. This push pull action further forces the proximal end of the connector 9 to be wedged in a friction tight manner against the interior wall 18. In this regard, the connector 9 is wedged against the interior wall 18 in such a friction tight manner that dislodgement or movement of the I.V. connected catheter from the venipuncture site protector 10 is only possible by pulling the tubing downwardly through the tube access slot 13 of the securement 12. This of course is only made possible by removing the securement 12 from the venipuncture site 11.

Figure 26:
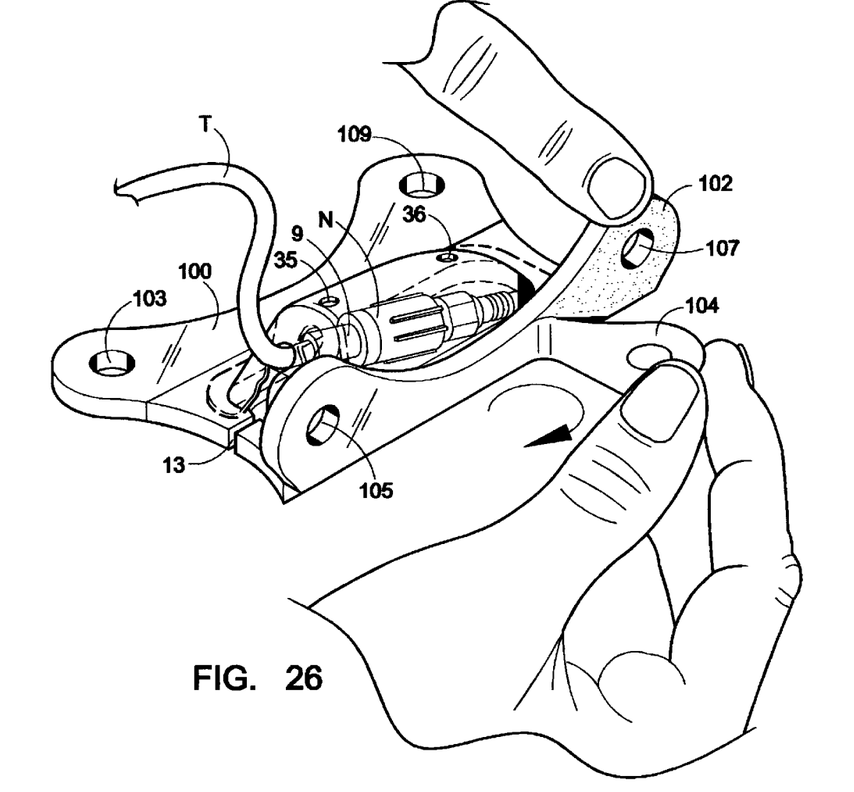

As best seen in FIG. 26, with the catheter 8 wedged within the venipuncture site protector 10, the health care provider lifts one of the lateral sides of the site protector 10 upward a sufficient distance so the protective cover 104 disposed on the underside of the securement 12 can be peeled away exposing the adhesive 102. The lifted lateral side is then pressed downward onto the skin of the patient to further secure the site protector 10 to the patient.

The health care provider then repeats the above mentioned procedure by lifting the other one of the lateral sides of the site protector 10 upward a sufficient distance so the remaining portion of the protective cover 104 disposed on the underside of the securement 12 can also be peeled away to exposed the adhesive 102. The other lifted lateral side is then pressed downward onto the skin of the patient to further secure the site protector 10 to the patient.

From the foregoing, it should be understood by those skilled in the art, that I.V. connected catheter is completely disposed within the front space 15 of the site protector 10 and completely immobilized therein due do the friction tight engagement of the connector 9 with the interior wall 18 and the capturing of the I.V. tubing T within the tube receiving stop 19. In short, both the I.V. connected catheter and the I.V. tubing T immediately adjacent the connector 9 are completely enclosed within the dome 24 and only the tubing T adjacent to the tubing T captured in the front wall tube stop 52 is extending out from the front wall 30. In this regard, the tubing T can not be dislodged from the site protector 10 except by exerting a sufficiently strong downward pulling action to dislodge the tubing T from both stops 20 and 52 so the tubing T can enter the slots 44 and 19, which in turn continue to exert a strong frictional resistance against the tubing so that dislodging the connector 9 from the interior wall 18 and the front wall 30 is extremely difficult if not entirely impossible, unless the site protector 10 is first removed from the skin of the patient so the tubing T can first be pulled downward through the tube access slot 13 of the securement 12.

As a final step, as best seen in FIG. 1, any excess tubing associated with the I.V. set T can then be taped to the hand of the user by using a non skin irritating tape 21.

Considering now the venipuncture protector 10 in still greater detail, as best seen in FIG. 2–3, the rear wall 28 has a convex tapered shaped extending from the apex 26 to the rear portion 40 of the flange 22. A pair of spaced apart ventilation holes 35 and 36 is disposed along the top of the dome 24 in the rear wall 28. The ventilation holes 35 and 36 allow the ventilation site 11 to breath so that the interior surface of the dome 24 will not accumulate unwanted moisture.

Another important feature of this embodiment of the present invention is that the front wall 30 slopes or slants upward toward the apex an angle $\alpha$, as best seen in FIG. 2, from the vertical. The angle $\alpha$ is preferably between about 50 degree to about 60 degrees. A more preferred angle $\alpha$ is between about 55 degrees to about 60 degrees, while the most preferred angle alpha is about 60 degrees. This feature is important since to dislodge the tubing of the I.V. set T from the site protector 10 becomes sequenced. That is, the tube must first be released from the tube-anchoring stop 52 disposed in the front wall 30, and then by continuing to pull downwardly on the tubing it can be released from the tube-anchoring stop 20 disposed in the interior wall 19.

Another important feature of this embodiment of the present invention is that the body member 14 slopes or slants at an angle $\beta$, as best seen in FIG. 27, from the horizontal or perpendicular to the normal plane P. The angle $\beta$ is preferably between about 20 degrees to about 30 degrees. A more preferred angle $\beta$ is between about 25 degrees to about 30 degrees, while the most preferred angle $\beta$ is about 30 degrees. This feature is important since the angle of the rear wall 28 allow the catheter 8 to be pulled upwardly from the venipuncture site 11 only a sufficient distance to allow the connector 9 to be wedged in a friction tight manner against the internal wall 18 and the tubing of the I.V. set T to be captured with the tube anchoring stops 220 and 52 respectively. In short, the catheter 8 is anchored in place within the interior of the venipuncture protector 10 and cannot be pulled out of the venipuncture site 10 unless the securement 12 is pulled from the skin of the patient.

As mentioned earlier, the overall length, height and width dimensions of an I.V. connected catheter are standardized in the medical industry. In this regard, the overall length of the dome 24 is select to be about 2.5 inches in lenth, while the maximum height of the dome 24 is selected to be about 0.8 inches. The length of the dome from it front wall edge at the flange 22 to the base of the internal wall 18 is about 0.6 inches. The width of the I.V. connected catheter at about the nut N is about 0.428 inches and the length of N is about 0.5400 inches. Based on the foregoing, the maximum angle of inflection that can be achieved in lifting the I.V. connected catheter from the venipuncture site 11 is about 12.5 degrees from the horizontal plane. This angle of inflection is substantially less than the angle $\beta$ as best seen in FIG. 27.

Figures 10, 11:
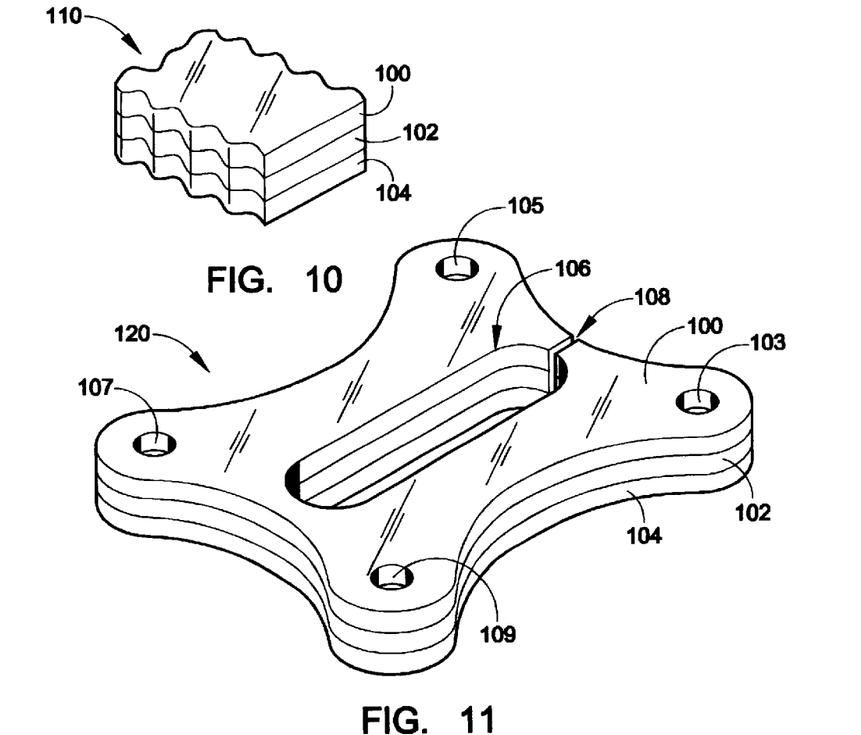
FIGS. 10–22 illustrate the steps of making the venipuncture site protector of FIG. 1.

Considering now the method of making the venipuncture protector 10 with reference to FIGS. 10–22, the method begins by first preparing a sheet of stock material 110 having a single adhesive surface that is protected by a wax paper covering. In this regard, the sheet of stock material 110 is prepared by providing a thin sheet of plastic material 100 having an upper surface area and a lower surface area as best seen in FIG. 10. The thin sheet of plastic material has a generally rectangular shape and a thickness of between about 3 mils and about 8 mils. The sheet of plastic material 100 is selected to have a sufficient surface area to be conformed into a desired shape corresponding to a desired securement shape, such as the securement shapes illustrated in FIGS. 5–8.

Next, the lower surface area of the sheet of plastic material 100 is coated with a thin layer of non-skin irritating adhesive 102, which in turn, is immediately covered with a thin sheet of covering material 104. The covering material 104 is selected to have a surface area that corresponds to the surface area of the thin sheet of plastic material 100 and is provided to protect the adhesive 102 from exposure to objects during the manufacturing process.

The prepared sheet of stock material 110 is then stamp cut into any one of the desired securement shapes previously mentioned or any other shape that would be desired. For example the prepared sheet of stock material 110 is stamp cut into a butterfly shape to form a securement base 120 as best seen in FIG. 11.

The process of making the butterfly shaped securement base 120 begins by first cutting the sheet of prepared material 110 into an overall desired securement shape, such as the butterfly shape as best seen in FIG. 11.

Next an elongated oval shaped hole indicated generally 106, is stamp cut through the sheet of stock material 110. The hole 106 is centrally disposed in the vertical plane of the butterfly shaped base 120, but slightly offset in the horizontal plane. A small access channel or slot 108 is then cut into the stock material that extends from its outer periphery boundary into the hole 106. In this regard, the access channel 108 is provided along an imaginary line L that bisects the butterfly shaped base 120 into two equal halves.

Next a plurality of aeration holes, such as aeration holes 103, 105, 107 and 109, are stamp cut through the sheet of stock material 110. The aeration holes 103, 105, 107, and 109 are equally spaced apart and positioned to be at about adjacent each of the corners of the butterfly shaped base 120. Although the method of preparing the butterfly shaped base 120 with the holes 103, 105, 106, 107, 109 and access channel 108 has been describes in individual stamp cutting steps, those skilled in the art will appreciate that the butterfly shaped base 120 can be prepare in a single stamp process as well.

The method of making the venipuncture protector 10 continues by angle cutting a pair of score lines, such as a score line 112, into covering material 104 disposed on the butterfly shaped base 120. It is important to note that the score line depth is sufficient to cut through the covering material 104 but not sufficient deep to enter into the adhesive layer 102.

Figure 12:
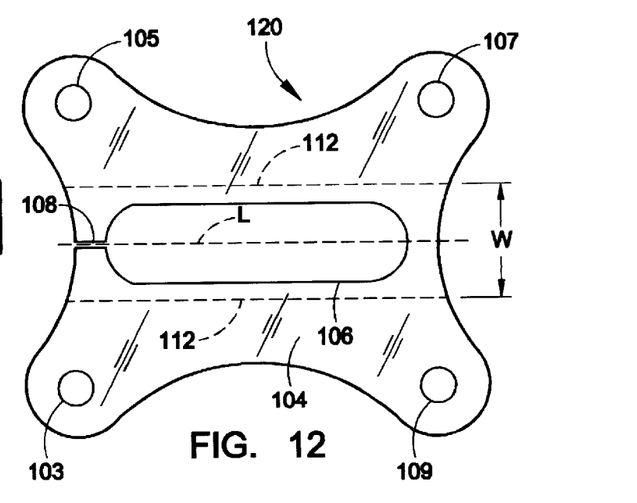
Figure 13:
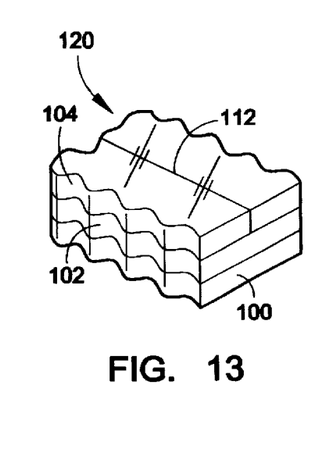

As best seen in FIGS. 12–13, each score line is spaced from a lateral edge of the elongated hole 106 and extends from one peripheral edge to the over peripheral edge of the covering material parallel to the lateral edges of the elongated oval shaped hole 106. In this regard, the score lines are spaced apart by a distance W, where the distance W is slightly greater than the width dimension of the plastic dome like shield 14.

Figure 14:
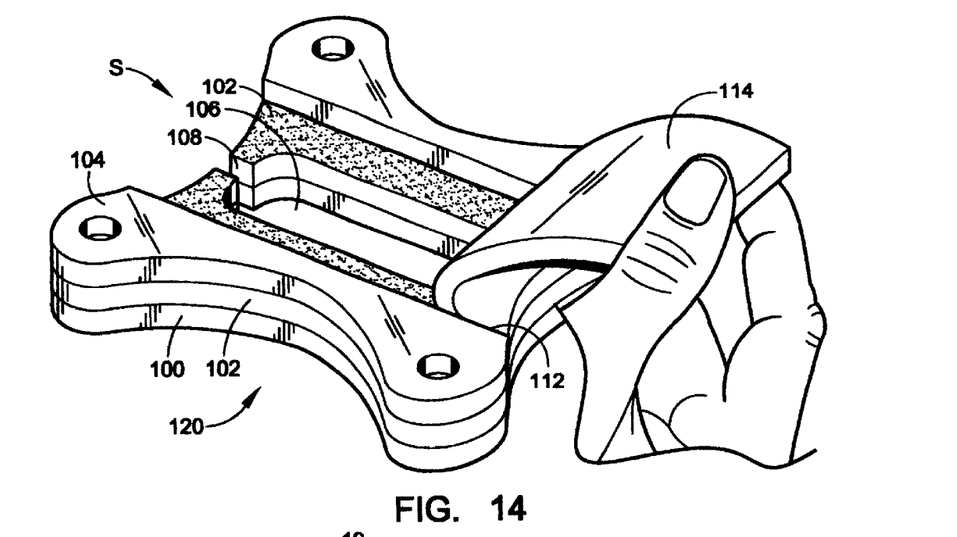

Next, as illustrated in FIG. 14, a single piece 114 of the covering material 104 whose lateral edges are defined by the score lines 112 is removed to form a void or space S within the bottom of the base 120. This step also exposes the adhesive layer 102 that surrounds the hole 106 and the access channel 108.

Figure 15:
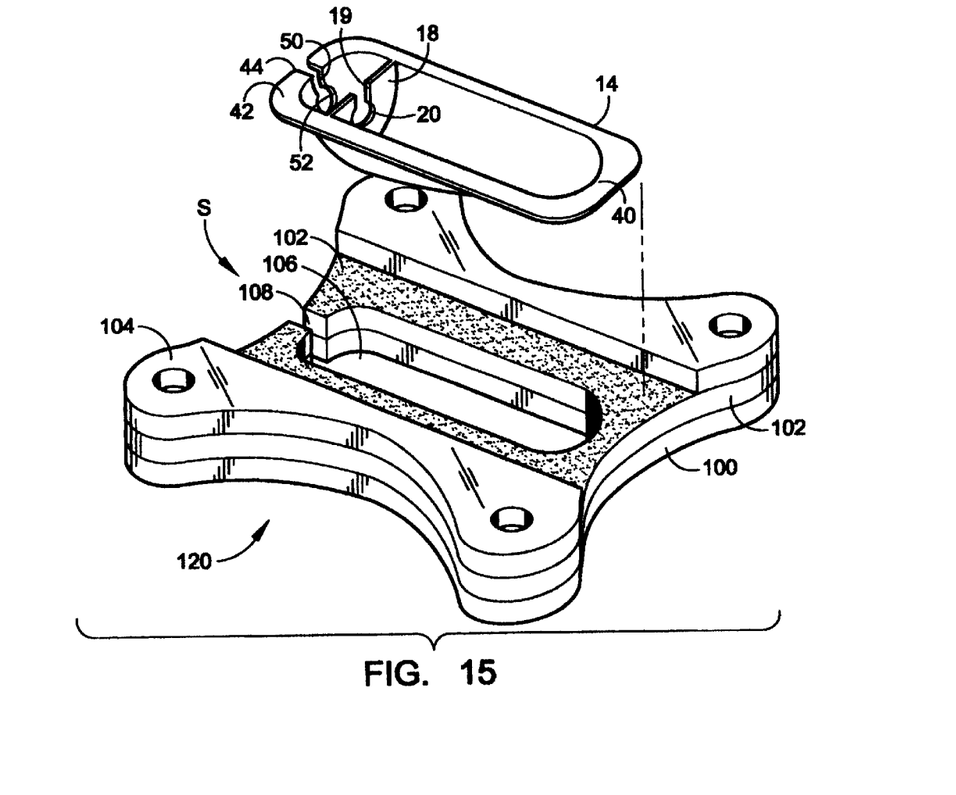

As best seen in FIG. 15, the method of making the venipuncture protector 10 continues by inverting the plastic shield 14 and then placing the plastic shield 14 into the oval shaped hole 106 so that the access channel of the shield 14 is aligned with the access channel 108. As the inverted shield 14 is dropped into the hole 106, the upper surface area of its flange 22 is secured by the adhesive layer 102 to the base 120.

Figure 16:
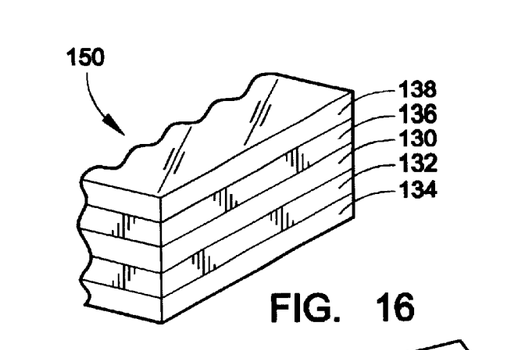
Figure 17:
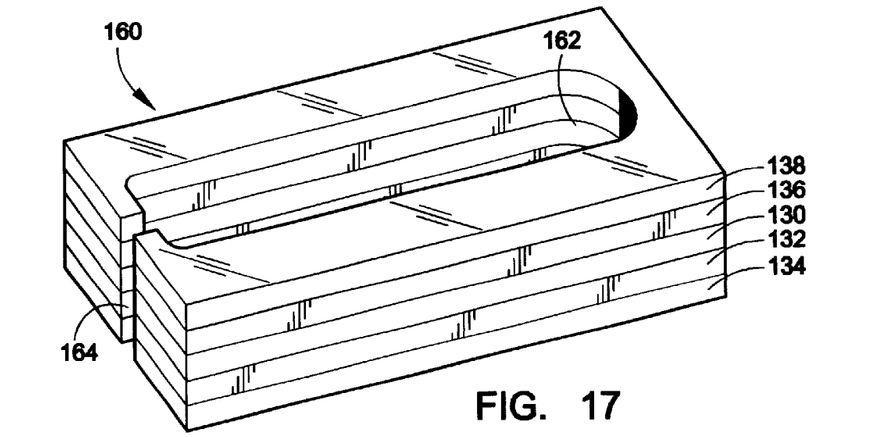

Next another sheet of stock material 150 having a two adhesive surfaces each surface being protected by a wax paper coverings is provided. In this regard, the sheet of stock material 150 is prepared by providing a thin sheet of plastic material 130 having an upper surface area and a lower surface area as best seen in FIG. 16. The thin sheet of plastic material 130 has a generally rectangular shape and a thickness of between about 3 mils and about 8 mils. The sheet of plastic material 130 is selected to have a sufficient surface area to be conformed into a desired shape corresponding to a surface area of the shield 14 as seen in a bottom plane view as best seen in FIG. 17.

Next, the lower surface area of the sheet of plastic material 130 is coated with a thin layer of adhesive 132, which in turn, is immediately covered with a thin sheet of covering material 134. The covering material 134 is selected to have a surface area that corresponds to the surface area of the thin sheet of plastic material 130 and is provided to protect the adhesive 132 from exposure to objects during the manufacturing process.

Next, the upper surface area of the sheet of plastic material 130 is coated with a thin layer of adhesive 136, which in turn, is immediately covered with a thin sheet of covering material 138. The covering material 138 is selected to have a surface area that corresponds to the surface area of the thin sheet of plastic material 130 and is provided to protect the adhesive 136 from exposure to objects during the manufacturing process.

Figure 19:
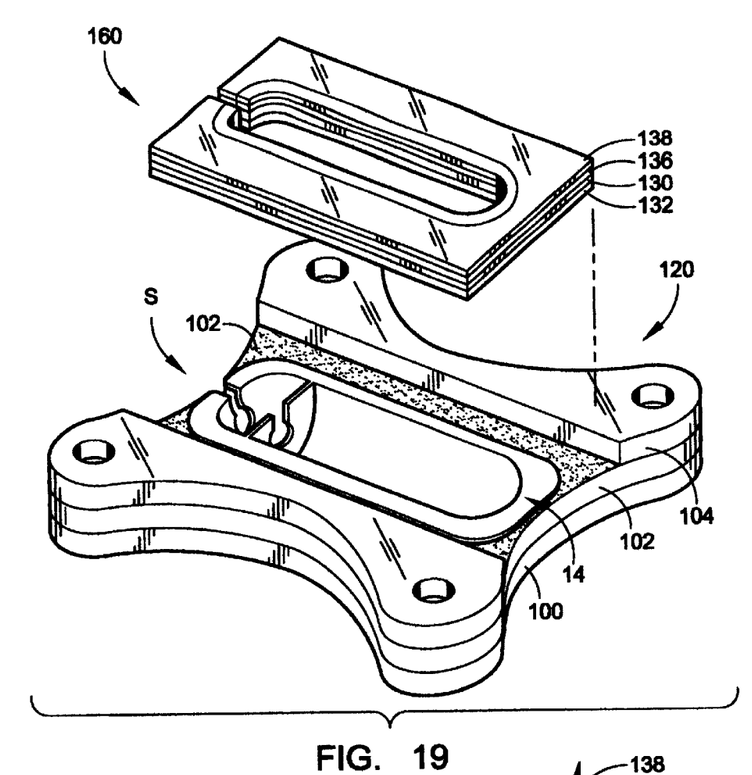

The prepared sheet of stock material 150 is then stamp cut into a plug 160 (FIG. 19) that substantially conforms to the shape of the dome like shield 14 as seen in a bottom plane view but with a surface area that is slightly larger. As best seen in FIG. 19 the plug 160 has sufficient width, height and depth dimensions to be received in and to fill the void or space S that was created when the single piece 114 of the covering material 114 was removed from the base 120. As best seen in FIG. 19, the plug 160 includes a hole 162 that correspond in shape to the hole 106 and a small access channel 164 that corresponds in shape to the access channel 108.

Figure 18:
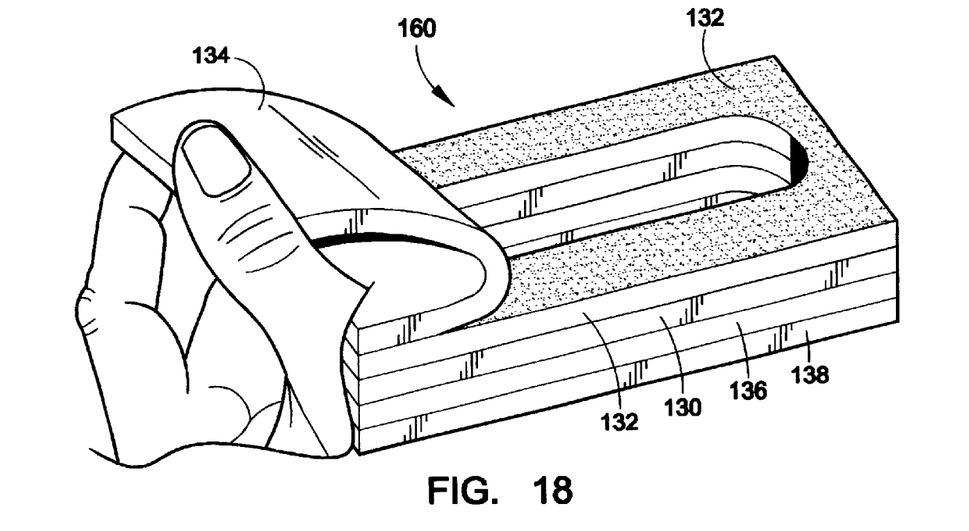

Next as best seen in FIG. 18, the plug 160 is inverted to expose the protective cover 134. The protective cover 134 disposed on the lower adhesive layer 136 is then removed, exposing the adhesive layer 136.

The plug 160 is then again inverted as best seen in FIG. 19, and moved into overlaying engagement with the exposed flange 22 of the shield 14 that was previously mounted to the base 120. In this regard, the plug 160 is moved into the space S and pressed against the undersurface of the shield 14 and against the base 120 to secure the shield 14 between the base 120 and the plug 160. In short then, the plug 160 is utilized to cover and secure the shield 14 to the base 120.

Figure 20:
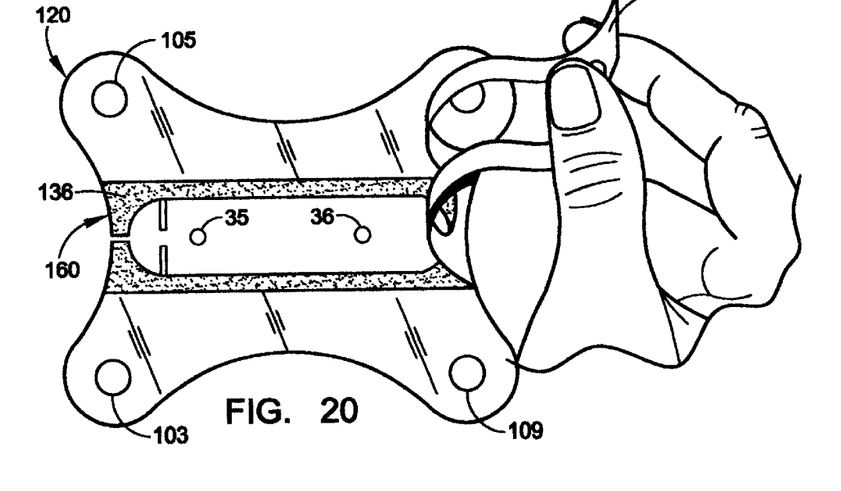

Next, as best seen in FIG. 20, the protective sheet 138 disposed on the upper layer of adhesive material 136 is removed, exposing the adhesive material 136.

As best seen in FIG. 21, the method of making the venipuncture protector 10 continues by providing another sheet of protecting covering, such as a wax paper covering 17. In this regard a stock sheet of wax paper is stamp cut into a desired cover shaped form. The desired cover shaped form is generally rectangular having a width dimension to overlay the exposed adhesive surface 136 of the stock material 160 and part of the base 120. The length dimension of the wax paper covering 17 is slightly greater than the length dimension of the base 120.

Figure 22:
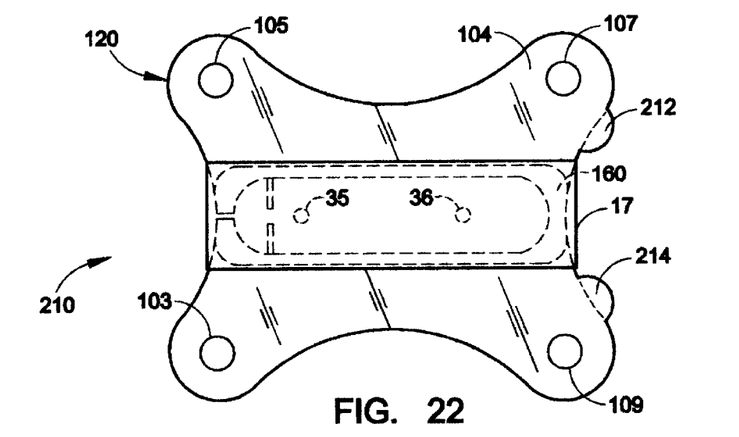
Figure 23:
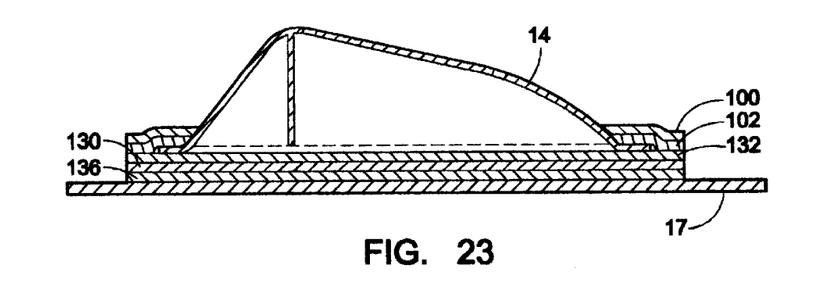
FIG. 23 is a cross sectional view of the venipuncture site protector of FIG. 21 taken along line 23—23.

As best seen in FIG. 22, another venipuncture protector 210 is shown and which is constructed in substantially in the same manner as the venipuncture protector 10 except the wax paper covering 104 is provided with a set of spaced apart lifting ears, such as the ears 212 and 214. The lifting ears 212 and 214 are sufficiently spaced apart from one another to not be covered by the wax paper covering 17.

Figure 6:
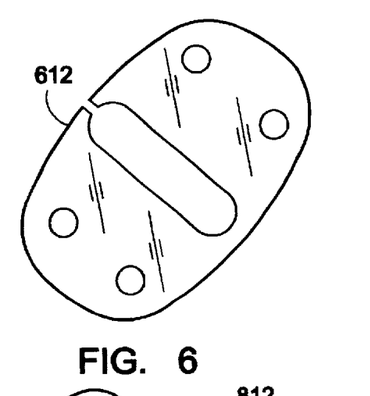
FIGS. 6–8 are illustrations of other types of securement configurations for use with the protective dome of FIG. 4.
Figure 7:
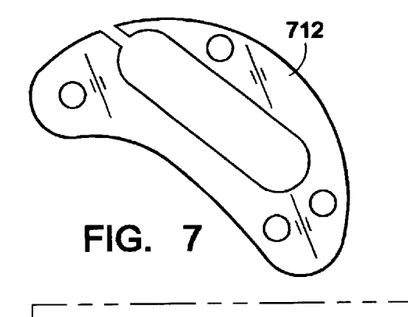
Figure 8:
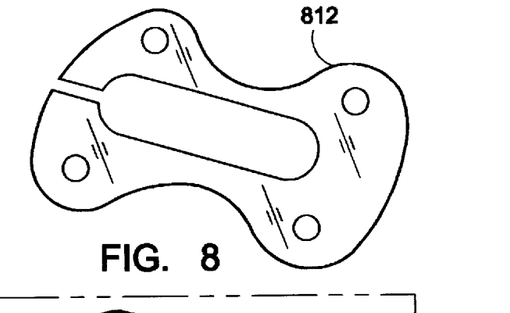

Referring now to the drawings and more particularly to FIGS. 6–8, there are illustrated other types of securements 612, 712, and 812. The securements 612, 712, and 812 are made and utilized in the same manner as securement 12 or 512. In this regard, there is no intention of limiting the scope of the present invention to any specific securement shape. In this regard, the securement shapes illustrated in FIGS. 6–8, as well as other types of securement shapes are contemplated within the true scope and spirit of the present invention.

Figure 9:
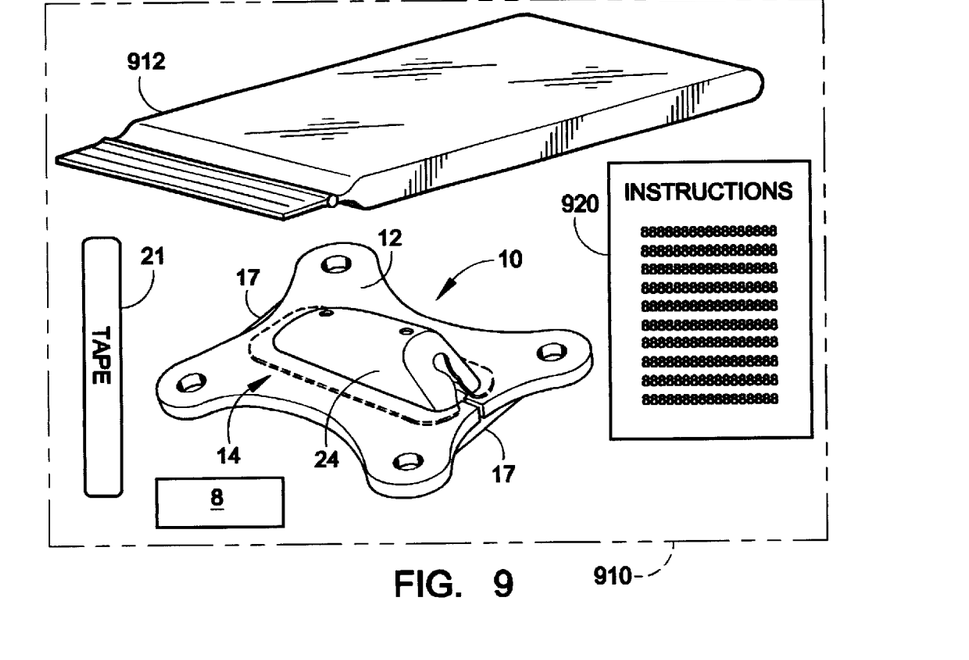
FIG. 9 is a venipuncture site protector kit, which is constructed in accordance with the present invention.

Referring now to the drawings and more particularly to FIG. 9 thereof, there is illustrated a site protector kit 910, which is constructed in accordance with another preferred embodiment of the present invention. The site protector kit 910 includes all of the necessary components to create a venipuncture site, such as the venipuncture site 11 and to protect that site 11 once a catheter C has been inserted into the vein of a patient. In this regard, the site protector kit 910 generally includes a sealed and sterilized packaging container 912 having disposed therein a venipuncture site protector 10, a set of instruction describing how to apply the venipuncture site protector 10 over a venipuncture site, a sealed and sterilized packaging container having a catheter 8 disposed therein, and a strip of tape 21 for securing any excess I.V. tubing to the area immediately adjacent to the venipuncture site 11.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

We claim:

1. A shielding device for an I.V. connected catheter, comprising:
    a securement having a tube receiving slot at one of its ends;
    a dome mounted to said securement, said dome having a rear wall and a front wall, said front wall having another tube receiving slot wherein said slot terminates at its upper boundary limit in a tube-anchoring stop;
    an internal wall disposed between said rear wall and said front wall for dividing said dome into a catheter receiving space and a tube receiving space, said internal wall having a tube access channel wherein said access channel terminates at its upper boundary limit in another tube anchoring stop; and
    said tube receiving slot, said another tube receiving slot and said tube access channel being in substantial alignment with one another to facilitate receiving and securing an I.V. tube within both said tube anchoring stop and said another tube anchoring stop as a proximal end portion of the I.V. connected catheter is wedged against said internal wall in friction tight engagement within said catheter receiving space.

2. The shielding device according to claim 1, wherein said securement has a lower surface area and an upper surface area, said lower surface area being coated with a layer of non-skin irritating adhesive to help facilitate anchoring the securement to a venipuncture site associated with the I.V. connected catheter.

3. The shielding device according to claim 2, further comprising;

a plurality of protective covers overlaying said layer of non-skin irritating adhesive.

4. The shielding device according to claim 1, wherein said slotted securement includes:
    a base securement having a base tube receiving slot and a lower surface coated with a layer of non-skin irritating adhesive to help facilitate anchoring the base securement to a venipuncture site associated with the I.V. connected catheter;
    said layer of non skin irritating adhesive being partially protected by a pair of spaced apart protective covers; and
    a plug having a plug tube receiving slot, said plug being disposed between said pair of spaced apart protective covers for helping to secure said dome to said base securement.

5. The shielding device according to claim 4, wherein said plug has a lower surface coated with a layer of non-skin irritating adhesive to further help facilitate anchoring the securement to the venipuncture site associated with the I.V. connected catheter.

6. The shielding device according to claim 5, wherein said layer of non-skin irritating adhesive disposed on the lower surface of said plug is protected by a removable protective cover.

7. The shielding device according to claim 5, wherein said plug slot and said base securement slot are in substantially parallel alignment with one another.

8. The shielding device according to claim 1, wherein said rear wall and said front wall meet an at a dome apex.

9. The shielding device according to claim 8, wherein said internal wall depends from said dome apex.

10. The shielding device according to claim 8, wherein said internal wall and said rear wall are disposed at about an angle $\alpha 0$ relative to one another at said dome apex to help limit the distance the I.V. connect catheter can be pulled up toward said rear wall.

11. The shielding device according to claim 10, wherein said angle $\alpha$ is between about 25 degrees and about 35 degrees.

12. The shielding device according to claim 10, wherein a most preferred angle $\alpha$ is about 30 degrees.

13. The shielding device according to claim 8, wherein said internal wall and sid front wall are disposed at abut an angle $\beta$ relative to one another at said dome apex to help secure an I.V. tube connected to the I.V connected catheter at two independent points wherein one point is completely covered by said dome.

14. The shielding device according to claim 13, wherein said angle $\beta$ is between about 55 degrees and about 65 degrees.

15. The shielding device according to claim 13 wherein a most preferred angle $\beta$ is about 60 degrees.

16. The shielding device according to claim 1, wherein dome includes a flange, said flange having a tube receiving slot disposed at one of its longitudinal ends.

17. The shielding device according to claim 1, wherein said front wall tube receiving slot terminating in a tube-anchoring stop and said internal wall with another tube receiving slot terminating in another tube anchoring stop are sufficiently space apart to secure at least two different portions of an I.V. tube disposed adjacent to and in fluid communication with the I.V. connected catheter.

18. The shielding device according to claim 1 wherein said dome includes a flange, said flange being integrally connected to said front wall and said rear wall;
    said flange having a flange tube receiving slot at one of its ends wherein said flange tube receiving slot is aligned with said front wall tube receiving slot.

19. The shielding device according to claim 1, wherein said internal wall creates a rear dome space and a front dome space;

said rear dome space being substantially larger that said front dome space;

said rear dome space being dimensioned to receive therein the I.V. connected catheter so that the I.V. connected catheter is completely covered by said dome.

20. A method of anchoring an I.V. connected catheter and its associated I.V. tubing, comprising the steps of:

providing a venipuncture site protector having a securement with a tube receiving slot at one of its ends; a hollow dome mounted to said securement, said dome having a rear wall, a front wall with a front wall tube receiving slot terminating in a tube-anchoring stop and an internal wall with another tube receiving slot terminating in another tube anchoring stop; said tube receiving slot, said front wall tube receiving slot and said another tube receiving slot being in substantial parallel alignment with one another; and said internal wall dividing the space within said hollow dome into a tube receiving compartment and an I.V. connected catheter compartment;

aligning a proximal end of the I.V. connected catheter within said I.V. connected catheter compartment so said proximal end is in alignment with said another tube receiving slot;

aligning the I.V. tubing disposed adjacent to the I.V. connected catheter to be received with said tube receiving slot, said front wall tube receiving slot and said another tube receiving slot;

partially securing said securement to a venipuncture site associated with the I.V. connected catheter allowing the I.V. tubing to be received within said tube receiving slot, said front wall tube receiving slot and said another tube receiving slot;

pressing down on said dome to hold it in place over the venipuncture site and then pulling up on said I.V. tubing at about its distal end until different portions of the I.V. tubing are respectively captured and secured within said tube anchoring stop and said another tube anchoring stop with the I.V. connected catheter wedged in friction tight engagement with said internal wall; and securing the lateral side portions of said securement to said venipuncture site.

\* \* \* \* \*